(12) United States Patent
Harlev et al.

(10) Patent No.: US 11,471,216 B2
(45) Date of Patent: Oct. 18, 2022

(54) CATHETER INSERTION

(71) Applicant: Affera, Inc., Watertown, MA (US)

(72) Inventors: Doron Harlev, Brookline, MA (US); Andrew Miles Wallace, Needham, MA (US); Luke Tsai, Clifton Park, NY (US); Ian Matthew Collier, Newton, MA (US)

(73) Assignee: Affera, Inc., Newton, MA (US)

( * ) Notice: Subject to any disclaimer, the term of this patent is extended or adjusted under 35 U.S.C. 154(b) by 142 days.

(21) Appl. No.: 15/584,080

(22) Filed: May 2, 2017

(65) Prior Publication Data
US 2017/0312020 A1      Nov. 2, 2017

Related U.S. Application Data

(60) Provisional application No. 62/330,395, filed on May 2, 2016, provisional application No. 62/357,704, filed
(Continued)

(51) Int. Cl.
    *A61B 18/14*      (2006.01)
    *A61B 18/12*      (2006.01)
    (Continued)

(52) U.S. Cl.
    CPC ...... *A61B 18/1492* (2013.01); *A61B 1/00087* (2013.01); *A61B 5/6843* (2013.01);
    (Continued)

(58) Field of Classification Search
    CPC .............. A61M 21/0662; A61M 21/01; A61M 3/0295; A61M 25/001; A61M 25/007;
    (Continued)

(56) References Cited

U.S. PATENT DOCUMENTS 5,281,218 A    1/1994   Imran
5,309,910 A    5/1994   Edwards et al.
(Continued)

FOREIGN PATENT DOCUMENTS

CN     101856271 A    10/2010
CN     104812297 A     7/2015
(Continued)

OTHER PUBLICATIONS

Kumar, et al., "Better Lesion Creation and Assessment During Catheter Ablation", Journal of Atrial Fibrillation, vol. 8, Issue 3, Oct.-Nov. 2015 , 12 Pages.
(Continued)

*Primary Examiner* — Eun Hwa Kim
*Assistant Examiner* — Catherine Premraj
(74) *Attorney, Agent, or Firm* — Perkins Coie LLP

(57) ABSTRACT

Devices, systems, and methods of the present disclosure can overcome physical constraints associated with catheter introduction to facilitate the use of a catheter with a large distal portion as part of a medical procedure benefiting from such a large distal portion, such as, for example, cardiac ablation. More specifically, devices, systems, and methods of the present disclosure can compress an expandable tip of a catheter from an expanded state to a compressed state along a tapered surface of an insertion sleeve for advancement of the expandable tip into vasculature of a patient. The tapered surface of the insertion sleeve can, for example, apply compressive forces at an angle against the advancing expandable tip. As compared to other approaches to the application of compressive force to an expandable tip, compressing the expandable tip using an angled force can reduce the likelihood of unintended deformation of the expandable tip.

17 Claims, 4 Drawing Sheets

Related U.S. Application Data on Jul. 1, 2016, provisional application No. 62/399,632, filed on Sep. 26, 2016, provisional application No. 62/399,625, filed on Sep. 26, 2016, provisional application No. 62/420,610, filed on Nov. 11, 2016, provisional application No. 62/424,736, filed on Nov. 21, 2016, provisional application No. 62/428,406, filed on Nov. 30, 2016, provisional application No. 62/434,073, filed on Dec. 14, 2016, provisional application No. 62/468,339, filed on Mar. 7, 2017, provisional application No. 62/468,873, filed on Mar. 8, 2017.

(51) Int. Cl.

| | | |
|---|---|---|
| *A61M 3/02* | (2006.01) | |
| *A61M 25/00* | (2006.01) | |
| *A61B 5/00* | (2006.01) | |
| *A61B 1/00* | (2006.01) | |
| *A61B 17/00* | (2006.01) | |
| *A61B 18/00* | (2006.01) | |
| *A61B 90/00* | (2016.01) | |

(52) U.S. Cl.
CPC ........ *A61B 5/6852* (2013.01); *A61B 18/1206* (2013.01); *A61B 18/1233* (2013.01); *A61B 18/14* (2013.01); *A61B 18/148* (2013.01); *A61B 18/1482* (2013.01); *A61M 3/0295* (2013.01); *A61M 25/001* (2013.01); *A61M 25/007* (2013.01); *A61M 25/0071* (2013.01); *A61M 25/0082* (2013.01); *A61B 2017/00039* (2013.01); *A61B 2017/00053* (2013.01); *A61B 2017/00154* (2013.01); *A61B 2017/00477* (2013.01); *A61B 2017/00526* (2013.01); *A61B 2017/00867* (2013.01); *A61B 2018/00011* (2013.01); *A61B 2018/0016* (2013.01); *A61B 2018/00029* (2013.01); *A61B 2018/00065* (2013.01); *A61B 2018/00077* (2013.01); *A61B 2018/00083* (2013.01); *A61B 2018/00089* (2013.01); *A61B 2018/0091* (2013.01); *A61B 2018/00101* (2013.01); *A61B 2018/00166* (2013.01); *A61B 2018/00214* (2013.01); *A61B 2018/00238* (2013.01); *A61B 2018/00267* (2013.01); *A61B 2018/00351* (2013.01); *A61B 2018/00357* (2013.01); *A61B 2018/00577* (2013.01); *A61B 2018/00642* (2013.01); *A61B 2018/00714* (2013.01); *A61B 2018/00726* (2013.01); *A61B 2018/00744* (2013.01); *A61B 2018/00767* (2013.01); *A61B 2018/00791* (2013.01); *A61B 2018/00797* (2013.01); *A61B 2018/00815* (2013.01); *A61B 2018/00821* (2013.01); *A61B 2018/00839* (2013.01); *A61B 2018/00875* (2013.01); *A61B 2018/00904* (2013.01); *A61B 2018/00982* (2013.01); *A61B 2018/00988* (2013.01); *A61B 2018/1417* (2013.01); *A61B 2018/1465* (2013.01); *A61B 2018/1467* (2013.01); *A61B 2090/061* (2016.02); *A61B 2090/065* (2016.02); *A61B 2090/376* (2016.02); *A61B 2090/3966* (2016.02); *A61B 2217/007* (2013.01); *A61B 2218/002* (2013.01); *A61B 2218/003* (2013.01); *A61M 2205/0266* (2013.01); *A61M 2207/00* (2013.01)

(58) Field of Classification Search
CPC .......... A61M 25/0071; A61M 25/0082; A61M 2205/0266; A61M 2207/00; A61B 18/1492; A61B 18/1206; A61B 18/1233; A61B 18/14; A61B 18/148; A61B 18/1482; A61B 1/00087; A61B 5/6843; A61B 5/6852; A61B 2090/061; A61B 2090/065; A61B 2090/376; A61B 2090/3966; A61B 2017/00039; A61B 2017/00053; A61B 2017/00154; A61B 2017/00577; A61B 2017/00526; A61B 2017/00867; A61B 2018/00011; A61B 2018/00029; A61B 2018/00065; A61B 2018/00077; A61B 2018/00083; A61B 2018/00089; A61B 2018/00101; A61B 2018/0016; A61B 2217/007; A61B 2218/002; A61B 2218/003

See application file for complete search history.

(56) References Cited

U.S. PATENT DOCUMENTS

| | | |
|---|---|---|
| 5,447,529 A | 9/1995 | Gottlieb et al. |
| 5,542,928 A | 8/1996 | Evans et al. |
| 5,588,432 A | 12/1996 | Crowley et al. |
| 5,722,403 A | 3/1998 | McGee et al. |
| 5,797,903 A | 8/1998 | Swanson et al. |
| 5,891,134 A | 4/1999 | Goble et al. |
| 5,891,136 A | 4/1999 | McGee et al. |
| 5,904,680 A | 5/1999 | Kordis et al. |
| 5,957,961 A | 9/1999 | Gaiser et al. |
| 5,968,040 A | 10/1999 | Swanson et al. |
| 6,014,579 A | 1/2000 | Pomeranz et al. |
| 6,036,689 A | 3/2000 | Tu et al. |
| 6,041,260 A | 3/2000 | Stern et al. |
| 6,053,913 A | 4/2000 | Tu et al. |
| 6,071,278 A | 6/2000 | Panescu et al. |
| 6,123,718 A | 9/2000 | Tu et al. |
| 6,142,993 A | 11/2000 | Whayne et al. |
| 6,165,169 A | 12/2000 | Panescu |
| 6,200,314 B1 | 3/2001 | Sherman |
| 6,246,913 B1 | 6/2001 | Sharkey |
| 6,315,778 B1 | 11/2001 | Gambale et al. |
| 6,369,465 B1 | 4/2002 | Swanson et al. |
| 6,416,511 B1 | 7/2002 | Lesh et al. |
| 6,537,248 B2 | 3/2003 | Mulier et al. |
| 6,572,612 B2 | 6/2003 | Stewart et al. |
| 6,632,223 B1 | 10/2003 | Keane |
| 6,658,279 B2 | 12/2003 | Swanson et al. |
| 6,813,520 B2 | 11/2004 | Truckai et al. |
| 6,917,834 B2 | 7/2005 | Koblish et al. |
| 6,923,805 B1 | 8/2005 | LaFontaine et al. |
| 7,519,410 B2 | 4/2009 | Taimisto et al. |
| 7,527,625 B2 | 5/2009 | Knight et al. |
| 7,993,337 B2 | 8/2011 | Lesh et al. |
| 8,221,407 B2 | 7/2012 | Swanson et al. |
| 8,235,988 B2 | 8/2012 | Davis et al. |
| 8,287,533 B2 | 10/2012 | Wittkampf et al. |
| 8,295,902 B2 | 10/2012 | Salahieh et al. |
| 8,348,937 B2 | 1/2013 | Wang et al. |
| 8,419,725 B2 | 4/2013 | Haemmerich et al. |
| 8,444,639 B2 | 5/2013 | Baxter et al. |
| 8,449,537 B2 | 5/2013 | Cao et al. |
| 8,449,539 B2 | 5/2013 | Wang et al. |
| 8,460,285 B2 | 6/2013 | Cao et al. |
| 8,500,730 B2 | 8/2013 | Lee et al. |
| 8,500,731 B2 | 8/2013 | Byrd et al. |
| 8,504,132 B2 | 8/2013 | Friedman et al. |
| 8,527,027 B2 | 9/2013 | Falwell et al. |
| 8,538,501 B2 | 9/2013 | Venkatachalam et al. |
| 8,545,408 B2 | 10/2013 | Morse et al. |
| 8,603,084 B2 | 12/2013 | Geurkink et al. |
| 8,636,732 B2 | 1/2014 | Davis et al. |
| 8,668,686 B2 | 3/2014 | Beeckler et al. |
| 8,702,690 B2 | 4/2014 | Cao et al. |
| 8,740,900 B2 | 6/2014 | Mirigian et al. |
| 8,764,742 B2 | 7/2014 | Hata et al. |
| 8,784,413 B2 | 7/2014 | Schwartz et al. |
| 8,790,341 B2 | 7/2014 | Hata et al. |

(56) References Cited

U.S. PATENT DOCUMENTS

| | | |
|---|---|---|
| 8,801,707 B2 | 8/2014 | Stewart et al. |
| 8,858,548 B2 | 10/2014 | Asconeguy et al. |
| 8,882,761 B2 | 11/2014 | Desai et al. |
| 8,900,228 B2 | 12/2014 | Grunewald et al. |
| 8,926,604 B2 | 1/2015 | Altmann et al. |
| 8,956,353 B2 | 2/2015 | Govari et al. |
| 8,974,453 B2 | 3/2015 | Wang |
| 8,986,292 B2 | 3/2015 | Morse et al. |
| 8,992,519 B2 | 3/2015 | Bencini et al. |
| 8,996,091 B2 | 3/2015 | de la Rama et al. |
| 9,011,432 B2 | 4/2015 | Kaufmann et al. |
| 9,037,264 B2 | 5/2015 | Just |
| 9,044,233 B2 | 6/2015 | Davis et al. |
| 9,084,611 B2 | 7/2015 | Armstrong et al. |
| 9,144,458 B2 | 9/2015 | Takaoka et al. |
| 9,155,587 B2 | 10/2015 | Willis et al. |
| 9,168,093 B2 | 10/2015 | Asconeguy et al. |
| 9,173,586 B2 | 11/2015 | Miller et al. |
| 9,226,791 B2 | 1/2016 | Kanowsky et al. |
| 9,241,756 B2 | 1/2016 | Berger et al. |
| 9,265,574 B2 | 2/2016 | Berger et al. |
| 9,314,299 B2 | 4/2016 | Fang |
| 9,339,325 B2 | 5/2016 | Teplitsky et al. |
| 9,352,134 B2 | 5/2016 | Reuveni et al. |
| 9,387,031 B2 | 7/2016 | Stewart et al. |
| 9,445,725 B2 | 9/2016 | Hettel et al. |
| 9,474,566 B2 | 10/2016 | Cao et al. |
| 9,492,227 B2 | 11/2016 | Jaramillo et al. |
| 9,510,892 B2 | 12/2016 | Davis et al. |
| 9,539,056 B2 | 1/2017 | Beeckler |
| 9,545,285 B2 | 1/2017 | Elolampi et al. |
| 10,105,179 B2 | 10/2018 | Harlev et al. |
| 10,219,860 B2 | 3/2019 | Harlev et al. |
| 2001/0020126 A1 | 9/2001 | Swanson et al. |
| 2001/0034518 A1 | 10/2001 | Edwards |
| 2002/0026094 A1 | 2/2002 | Roth |
| 2002/0198492 A1* | 12/2002 | Miller .................. A61M 25/10 604/96.01 |
| 2003/0018362 A1 | 1/2003 | Fellows et al. |
| 2003/0032953 A1 | 2/2003 | VanDusseldorp et al. |
| 2003/0083613 A1 | 5/2003 | Schaer |
| 2003/0093086 A1 | 5/2003 | Briggs et al. |
| 2003/0158477 A1 | 8/2003 | Panescu |
| 2004/0087936 A1 | 5/2004 | Stern et al. |
| 2004/0199156 A1 | 10/2004 | Rioux et al. |
| 2004/0215296 A1 | 10/2004 | Ganz et al. |
| 2004/0215310 A1 | 10/2004 | Amirana |
| 2004/0254621 A1 | 12/2004 | Jones et al. |
| 2005/0020914 A1 | 1/2005 | Amundson et al. |
| 2005/0171524 A1 | 8/2005 | Stern et al. |
| 2005/0171525 A1 | 8/2005 | Rioux et al. |
| 2005/0222563 A1 | 10/2005 | McDaniel et al. |
| 2005/0245876 A1* | 11/2005 | Khosravi ............ A61B 17/3431 604/164.1 |
| 2007/0016391 A1 | 1/2007 | Minoguchi |
| 2008/0009747 A1 | 1/2008 | Saadat et al. |
| 2008/0033421 A1 | 2/2008 | Davis et al. |
| 2008/0262489 A1 | 10/2008 | Steinke et al. |
| 2008/0281391 A1 | 11/2008 | MacAdam et al. |
| 2008/0287942 A1 | 11/2008 | Amundson et al. |
| 2009/0076498 A1 | 3/2009 | Saadat et al. |
| 2009/0093802 A1 | 4/2009 | Kulesa et al. |
| 2009/0171274 A1 | 7/2009 | Harlev et al. |
| 2009/0221965 A1 | 9/2009 | Osypka et al. |
| 2010/0030209 A1 | 2/2010 | Govari et al. |
| 2010/0057072 A1 | 3/2010 | Roman et al. |
| 2010/0057074 A1 | 3/2010 | Roman et al. |
| 2010/0145330 A1 | 6/2010 | Badie et al. |
| 2010/0152731 A1 | 6/2010 | de la Rama et al. |
| 2010/0168647 A1 | 7/2010 | Tegg et al. |
| 2010/0234807 A1* | 9/2010 | Fisher ............... A61M 39/0606 604/167.04 |
| 2010/0240995 A1 | 9/2010 | Nuccitelli et al. |
| 2010/0324540 A1* | 12/2010 | Paulen ............... A61M 25/0017 604/544 |
| 2011/0009857 A1 | 1/2011 | Subramaniam et al. |
| 2011/0022041 A1 | 1/2011 | Ingle et al. |
| 2011/0106012 A1* | 5/2011 | Velarde ................. A61M 25/04 604/164.03 |
| 2011/0118726 A1 | 5/2011 | Rama et al. |
| 2011/0160584 A1 | 6/2011 | Paul et al. |
| 2011/0201973 A1 | 8/2011 | Stephens et al. |
| 2011/0257649 A1 | 10/2011 | Geistert et al. |
| 2011/0270242 A1 | 11/2011 | Marion |
| 2012/0046610 A1 | 2/2012 | Rankin et al. |
| 2012/0101413 A1 | 4/2012 | Beetel et al. |
| 2012/0123400 A1 | 5/2012 | Francischelli et al. |
| 2012/0136350 A1 | 5/2012 | Goshgarian et al. |
| 2012/0157890 A1 | 6/2012 | Govari et al. |
| 2012/0165809 A1 | 6/2012 | Christian et al. |
| 2012/0165812 A1 | 6/2012 | Christian et al. |
| 2012/0172871 A1 | 7/2012 | Hastings et al. |
| 2012/0184863 A1 | 7/2012 | Harlev et al. |
| 2012/0209260 A1 | 8/2012 | Lambert et al. |
| 2012/0265192 A1 | 10/2012 | Sliwa et al. |
| 2012/0302877 A1 | 11/2012 | Harks et al. |
| 2012/0310064 A1 | 12/2012 | McGee et al. |
| 2013/0060245 A1 | 3/2013 | Grunewald et al. |
| 2013/0066315 A1 | 3/2013 | Subramaniam et al. |
| 2013/0085413 A1 | 4/2013 | Tsamir et al. |
| 2013/0096550 A1 | 4/2013 | Hill et al. |
| 2013/0137980 A1 | 5/2013 | Waters et al. |
| 2013/0190754 A1 | 7/2013 | Paul et al. |
| 2013/0282084 A1 | 10/2013 | Mathur et al. |
| 2013/0286012 A1 | 10/2013 | Medioni et al. |
| 2013/0296852 A1 | 11/2013 | Madjarov et al. |
| 2014/0012160 A1 | 1/2014 | Ghaffari et al. |
| 2014/0017639 A1 | 1/2014 | Zhang et al. |
| 2014/0058197 A1 | 2/2014 | Salahieh et al. |
| 2014/0058208 A1* | 2/2014 | Shafran ............... A61B 17/0218 600/207 |
| 2014/0058375 A1 | 2/2014 | Koblish et al. |
| 2014/0107639 A1 | 4/2014 | Zhang et al. |
| 2014/0121657 A1 | 5/2014 | Bar-Tai et al. |
| 2014/0142570 A1 | 5/2014 | Bakczewitz et al. |
| 2014/0163360 A1 | 6/2014 | Stevens-Wright et al. |
| 2014/0206985 A1 | 7/2014 | Kariv et al. |
| 2014/0228832 A1 | 8/2014 | Chun |
| 2014/0236146 A1 | 8/2014 | McLawhorn et al. |
| 2014/0257282 A1 | 9/2014 | Wang et al. |
| 2014/0276078 A1 | 9/2014 | Schweitzer et al. |
| 2014/0276562 A1 | 9/2014 | Govari et al. |
| 2014/0276617 A1* | 9/2014 | Akingba ............... A61M 25/01 604/510 |
| 2014/0316400 A1 | 10/2014 | Blix et al. |
| 2014/0316406 A1 | 10/2014 | Willis et al. |
| 2014/0357956 A1 | 12/2014 | Salahieh et al. |
| 2014/0364848 A1 | 12/2014 | Heimbecher |
| 2015/0018818 A1 | 1/2015 | Willard et al. |
| 2015/0105645 A1 | 4/2015 | Subramaniam |
| 2015/0105659 A1 | 4/2015 | Salahieh et al. |
| 2015/0119876 A1 | 4/2015 | Willard |
| 2015/0119883 A1 | 4/2015 | Buysman |
| 2015/0133920 A1 | 5/2015 | Rankin et al. |
| 2015/0141738 A1 | 5/2015 | Toellner et al. |
| 2015/0141982 A1 | 5/2015 | Lee |
| 2015/0202408 A1* | 7/2015 | McMurtry ........... A61B 17/0401 604/510 |
| 2015/0223757 A1 | 8/2015 | Werneth |
| 2015/0272667 A1 | 10/2015 | Govari et al. |
| 2015/0282859 A1 | 10/2015 | Bencini |
| 2015/0297292 A1 | 10/2015 | Sutermeister et al. |
| 2015/0327921 A1 | 11/2015 | Govari et al. |
| 2015/0327925 A1 | 11/2015 | Christian |
| 2015/0342671 A1 | 12/2015 | Govari et al. |
| 2015/0342672 A1 | 12/2015 | Bencini |
| 2015/0351836 A1 | 12/2015 | Prutchi |
| 2015/0366604 A1 | 12/2015 | Shikhman et al. |
| 2015/0374252 A1 | 12/2015 | de la Rama et al. |
| 2016/0051321 A1 | 2/2016 | Salahieh et al. |
| 2016/0058502 A1 | 3/2016 | Clark et al. |
| 2016/0174864 A1 | 6/2016 | Levin et al. |
| 2016/0184008 A1 | 6/2016 | Papaioannou et al. |
| 2016/0228023 A1 | 8/2016 | Govari |

(56) References Cited

U.S. PATENT DOCUMENTS

| | | |
|---|---|---|
| 2016/0278856 A1 | 9/2016 | Panescu et al. |
| 2016/0287312 A1 | 10/2016 | Tegg et al. |
| 2016/0331254 A1 | 11/2016 | Tegg et al. |
| 2016/0361115 A1 | 12/2016 | Bencini |
| 2016/0374754 A1 | 12/2016 | Asirvatham et al. |
| 2017/0312007 A1 | 11/2017 | Harlev et al. |
| 2017/0312008 A1 | 11/2017 | Harlev et al. |
| 2017/0312012 A1 | 11/2017 | Harlev et al. |
| 2017/0312023 A1 | 11/2017 | Harlev et al. |
| 2017/0312024 A1 | 11/2017 | Harlev et al. |
| 2017/0312025 A1 | 11/2017 | Harlev et al. |
| 2017/0312027 A1 | 11/2017 | Harlev et al. |
| 2017/0312028 A1 | 11/2017 | Harlev et al. |
| 2019/0076190 A1 | 3/2019 | Harlev et al. |

FOREIGN PATENT DOCUMENTS

| | | |
|---|---|---|
| EP | 1256326 | 11/2002 |
| EP | 1498080 | 11/2009 |
| EP | 2201905 | 6/2010 |
| EP | 1554986 | 9/2010 |
| EP | 2229904 | 9/2010 |
| EP | 2382935 | 11/2011 |
| EP | 2913017 | 9/2015 |
| EP | 2470099 | 10/2015 |
| EP | 3141181 | 3/2017 |
| JP | H0838503 A | 2/1996 |
| JP | 4062935 B2 | 3/2008 |
| JP | 2009-532162 A | 9/2009 |
| JP | 2012-520474 A | 9/2012 |
| WO | 0122897 A1 | 4/2001 |
| WO | WO-2004110258 | 12/2004 |
| WO | 2010056771 A1 | 5/2010 |
| WO | WO-2011101778 | 8/2011 |
| WO | WO-2014132463 | 9/2014 |
| WO | 2014168987 A1 | 10/2014 |
| WO | 2015200518 A1 | 12/2015 |
| WO | WO-2017192477 | 11/2017 |
| WO | WO-2017192480 | 11/2017 |
| WO | WO-2017192495 | 11/2017 |
| WO | WO-2017192510 | 11/2017 |
| WO | WO-2017192542 | 11/2017 |

OTHER PUBLICATIONS

Solazzo, Stephanie A. et al., "High-Power Generator for Radiofrequency Ablation: Larger Electrodes and Pulsing Algorithms in Bovine ex Vivo and Porcine in Vivo Settings", Experimental Studies; Radiology; vol. 242; No. 3, Mar. 2007, pp. 743-750.
Goldberg, S. N. et al., "Percutaneous Radiofrequency Tissue Ablation: Optimization of Pulsed-Radiofrequency Technique to Increase Coagulation Necrosis", JVIR; vol. 10 No. 7, Jul.-Aug. 1999, pp. 907-916.
MDDI, "Machining Materials: A Primer on Photoetching", Medical Service and Diagnostics Industry http://www.mddionline.com/article/machining-materials-primer-photoetching Jan. 1, 2008, 3 Pages.
USPTO, "U.S. Appl. No. 15/584,634 Final Office Action dated Oct. 16, 2017", 28 pages.
USPTO, "U.S. Appl. No. 15/584,825, Non-Final Office Action dated Aug. 28, 2017", 11 pages.
USPTO, "U.S. Appl. No. 15/584,634, Non-Final Office Action dated Aug. 18, 2017", 24 pages.
ISA, "PCT Application No. PCT/US17/30492 International Search Report and Written Opinion dated Jul. 25, 2017", 16 pages.
ISA, "PCT Application No. PCT/US17/30495 International Search Report and Written Opinion dated Nov. 15, 2017", 18 pages.
ISA, "PCT Application No. PCT/US17/30495 Invitation to Pay Additional Fees and Partial International Search Report dated Sep. 8, 2017", 14 pages.
ISA, "PCT Application No. PCT/US17/30518 International Search Report and Written Opinion dated Sep. 7, 2017", 15 pages.
ISA, "PCT Application No. PCT/US17/30535 International Search Report and Written Opinion dated Jan. 5, 2018", 15 pages.
ISA, "PCT Application No. PCT/US17/30535 Invitation to Pay Add'l Fees and Partial Search Report dated Sep. 14, 2017", 12 pages.
ISA, "PCT Application No. PCT/US17/30575 International Search Report and Written Opinion dated Nov. 15, 2017", 17 pages.
ISA, "PCT Application No. PCT/US17/30575 Invitation to Pay Additional Fees and Partial Search Report dated Sep. 20, 2017", 14 pages.
Byun et al., Radiofrequency Ablation of the Gastrointestinal Tract with a Stent-Like Electrode: Experimental Study, Koean J Radiol 4(1), Mar. 2003, pp. 19-26.
International Search Report and Written Opinion dated Nov. 15, 2017; International Application No. PCT/US2017/030575; 15 pages.
International Search Report and Written Opinion dated Nov. 15, 2017; International Patent Application No. PCT/US2017/030495; 16 pages.
International Search Report and Written Opinion dated Sep. 7, 2017; International Patent Application No. PCT/US2017/030518; 13 pages.
Koruth et al., Bipolar irrigated radiofrequency ablation: A therapeutic option for refractory intramural atrial and ventricular tachycardia circuits, Heart Rhythm, Dec. 2012, vol. 9, Issue 12, pp. 1932-1941.
Sapp et al., Deep Myocardial Ablation Lesions Can Be Created with a Retractable Nedele-Tipped Catheter, Pacing and Clinical Electrophysiology, vol. 27, Issue 5, May 2004, pp. 599-594.
International Search Report and Written Opinion dated Apr. 14, 2021 for International Patent Application No. PCT/US20/65314, 13 pages.

\* cited by examiner

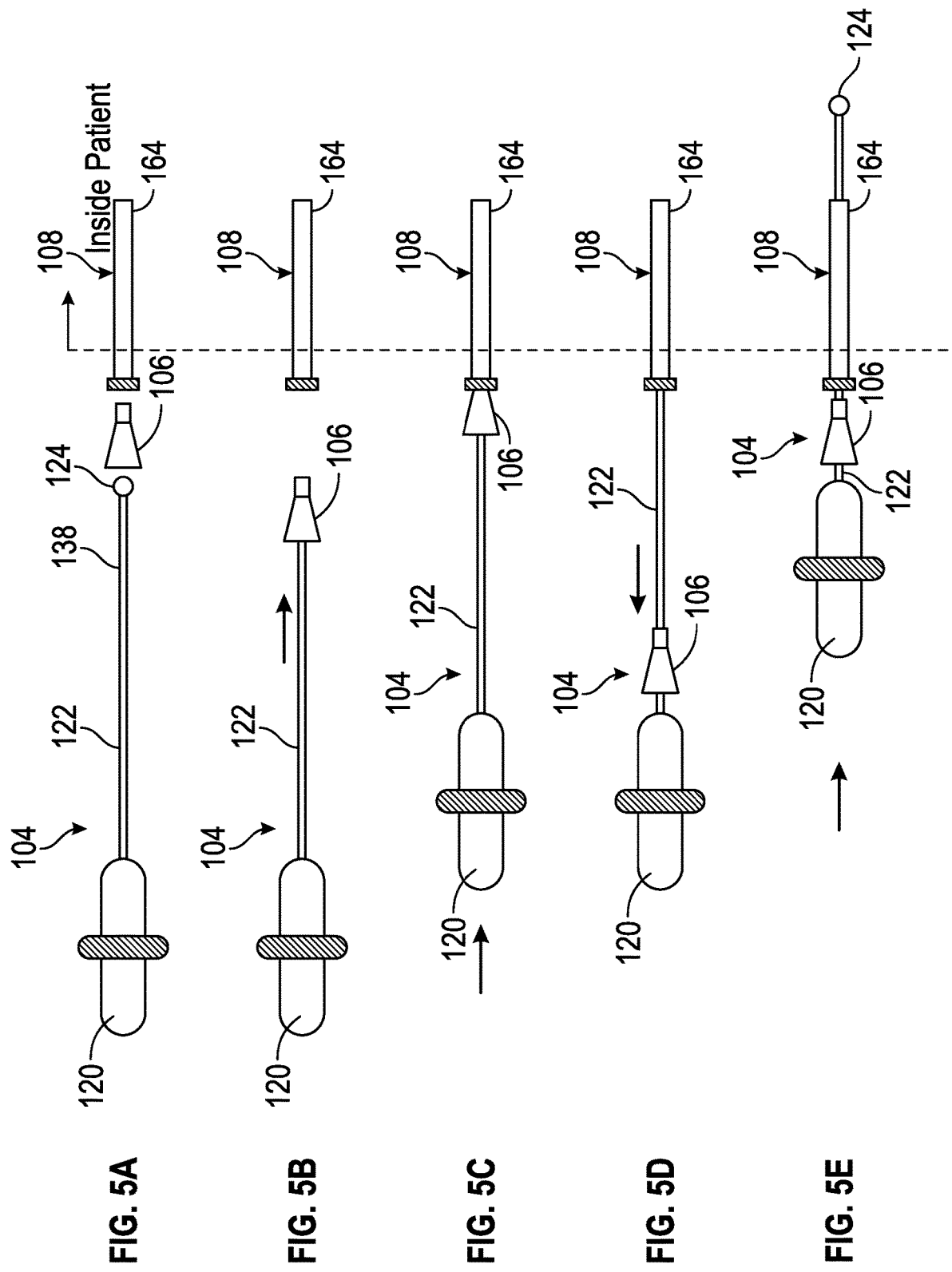

CATHETER INSERTION

CROSS-REFERENCE TO RELATED APPLICATIONS

This application claims the benefit under 35 U.S.C. § 119(e) of U.S. Prov. App. No. 62/330,395, filed May 2, 2016, U.S. Prov. App. No. 62/357,704, filed Jul. 1, 2016, U.S. Prov. App. No. 62/399,632, filed Sep. 26, 2016, U.S. Prov. App. No. 62/399,625, filed Sep. 26, 2016, U.S. Prov. App. No. 62/420,610, filed Nov. 11, 2016, U.S. Prov. App. No. 62/424,736, filed Nov. 21, 2016, U.S. Prov. App. No. 62/428,406, filed Nov. 30, 2016, U.S. Prov. App. No. 62/434,073, filed Dec. 14, 2016, U.S. Prov. App. No. 62/468,339, filed Mar. 7, 2017, and U.S. Prov. App. No. 62/468,873, filed Mar. 8, 2017, with the entire contents of each of these applications hereby incorporated herein by reference.

This application is also related to the following commonly-owned U.S. patent applications U.S. patent application Ser. No. 15/584,634, filed May 2, 2017, and entitled "CATHETER SENSING AND IRRIGATING"; U.S. patent application Ser. No. 15/584,323, filed May 2, 2017, and entitled "LESION FORMATION"; U.S. patent application Ser. No. 15/584,533, filed May 2, 2017, and entitled "PULSED RADIOFREQUENCY ABLATION"; U.S. patent application Ser. No. 15/584,146, filed May 2, 2017, and entitled "THERAPEUTIC CATHETER WITH IMAGING." Each of the foregoing applications is hereby incorporated herein by reference in its entirety.

BACKGROUND

Catheters are used for a variety of procedures related to diagnosis and treatment of medical conditions in patients. Physical limitations exist, however, with respect to the size of a catheter that can be introduced into a body of a patient. Such limitations can constrain the size of a distal portion of the catheter available for diagnosis or treatment at a location within the body of the patient.

SUMMARY

Devices, systems, and methods of the present disclosure can overcome physical constraints associated with catheter introduction to facilitate the use of a catheter with a large distal portion as part of a medical procedure benefiting from such a large distal portion, such as, for example, cardiac ablation. More specifically, devices, systems, and methods of the present disclosure can compress an expandable tip of a catheter from an expanded state to a compressed state along a tapered surface of an insertion sleeve for advancement of the expandable tip into vasculature of a patient. The tapered surface of the insertion sleeve can, for example, apply compressive forces at an angle against the advancing expandable tip. As compared to other approaches to the application of compressive force to an expandable tip, compressing the expandable tip using an angled force can reduce the likelihood of unintended deformation of, or damage to the expandable tip.

In one aspect, a method of inserting a catheter into vasculature of a patient includes positioning a distal portion of a sheath in a blood vessel of the patient, moving an insertion sleeve proximally over an expandable tip supported by a catheter shaft, the proximal movement of the insertion sleeve compressing at least one portion of the expandable tip from an expanded state to a compressed state along a tapered surface of the insertion sleeve, mating the insertion sleeve with the sheath, and advancing the expandable tip distally beyond the sheath and into the vasculature of the patient.

In certain implementations, the insertion sleeve can be mated with the sheath with the expandable tip disposed in the insertion sleeve in the compressed state.

In some implementations, at least one portion of the expandable tip in the expanded state can have a maximum radial dimension greater than a maximum radial dimension of the sheath.

In certain implementations, the at least one portion of the expandable tip can be resiliently flexible between the expanded state and the compressed state in response to addition and removal of external force applied to the at least one portion of the expandable tip.

In some implementations, the insertion sleeve can define a proximal opening and a distal opening, and the proximal opening is larger than the distal opening. For example, the at least one portion of the expandable tip can be collapsible from the expanded state to the compressed state through both distal movement of the expandable tip through the proximal opening of the insertion sleeve and through proximal movement of the expandable tip through the distal opening of the insertion sleeve. Additionally, or alternatively, the method can further include retracting the expandable tip proximally through the distal opening and collapsing the expandable tip from the expanded state to the compressed state.

In certain implementations, mating the insertion sleeve with the sheath can include positioning a portion of the insertion sleeve within a sheath lumen defined by the sheath. For example, mating the insertion sleeve with the sheath can include positioning a portion of the insertion sleeve in the sheath lumen at a position distal to a valve of the sheath. Additionally, or alternatively, the portion of the insertion sleeve positioned in the sheath lumen can be an elongate tube (e.g., tapered in a distal direction). Further, or instead, with the portion of the insertion sleeve in the sheath lumen at the position distal to the valve of the sheath, the sheath can block further distal movement of the insertion sleeve.

In some implementations, advancing the expandable tip distally beyond the sheath can include expanding the at least one portion of the expandable tip from the compressed state to the expanded state. For example, the at least one portion of the expandable tip is self-expandable from the compressed state to the expanded state.

In certain implementations, the sheath can have an 8 Fr diameter.

In some implementations, the tapered surface of the insertion sleeve can be substantially frusto-conical. Additionally, or alternatively, an included angle defined between the tapered surface and a center axis defined by the insertion sleeve can be greater than about 4 degrees and less than about 45 degrees.

In certain implementations, the method can further include removing the insertion sleeve from the catheter shaft while the at least one portion of the expandable tip is in the vasculature of the patient. For example, the insertion sleeve can include a break-away portion and removing the insertion sleeve from the catheter shaft can include removing the break-away portion from the insertion sleeve.

In certain implementations, the sheath can be one or more of an introducer sheath, a steerable sheath, and a fixed curve sheath.

In some implementations, the expandable tip can include one or more electrodes. For example, the expandable tip can be an ablation electrode.

In another aspect, a system can include a catheter including a shaft and an expandable tip disposed along a distal portion of the shaft, at least one portion of the expandable tip resiliently flexible between an expanded state and a compressed state, a sheath defining a sheath lumen, the at least one portion of the expandable tip, in the compressed state, movable through the sheath lumen, and an insertion sleeve including a tapered surface defining at least a portion of a sleeve lumen, the at least one portion of the expandable tip movable into engagement with the tapered surface, the engagement of the tapered surface compressing the at least one portion of the expandable tip from the expanded state to the compressed state as the at least one portion of the expandable tip is moved through the sleeve lumen in a direction toward the sheath lumen.

In certain implementations, the tapered surface of the insertion sleeve can be substantially frusto-conical. For example, an included angle defined between the tapered surface and a center axis defined by the sleeve lumen of the insertion sleeve can be greater than about 4 degrees and less than about 45 degrees. Additionally, or alternatively, the insertion sleeve can define a proximal opening and a distal opening, the proximal opening having a first open area to receive the at least one portion of the expandable tip in the expanded state and the distal opening having a second open area less than the first open area.

In some implementations, the at least one portion of the expandable tip can be proximally and distally movable through the insertion sleeve.

In certain implementations, the sheath can include a valve and the insertion sleeve can include an elongate tube, the insertion sleeve engageable with the sheath, and the elongate tube sized to extend beyond the valve with the insertion sleeve engaged with the sheath. The elongate tube can be, for example, tapered in a distal direction.

In some implementations, the sheath can include one or more of an introducer sheath, a steerable sheath, and a fixed curve sheath.

In certain implementations, the expandable tip can include one or more electrodes. For example, the expandable tip can be an ablation electrode.

Other aspects, features, and advantages will be apparent from the description and drawings, and from the claims.

BRIEF DESCRIPTION OF THE DRAWINGS

FIGS. 5A-5E are schematic representations of steps of an exemplary method of using the system of FIG. 1 to insert the expandable tip of the catheter of FIG. 2 into a patient.

Like reference symbols in the various drawings indicate like elements.

DETAILED DESCRIPTION

Figure 1:
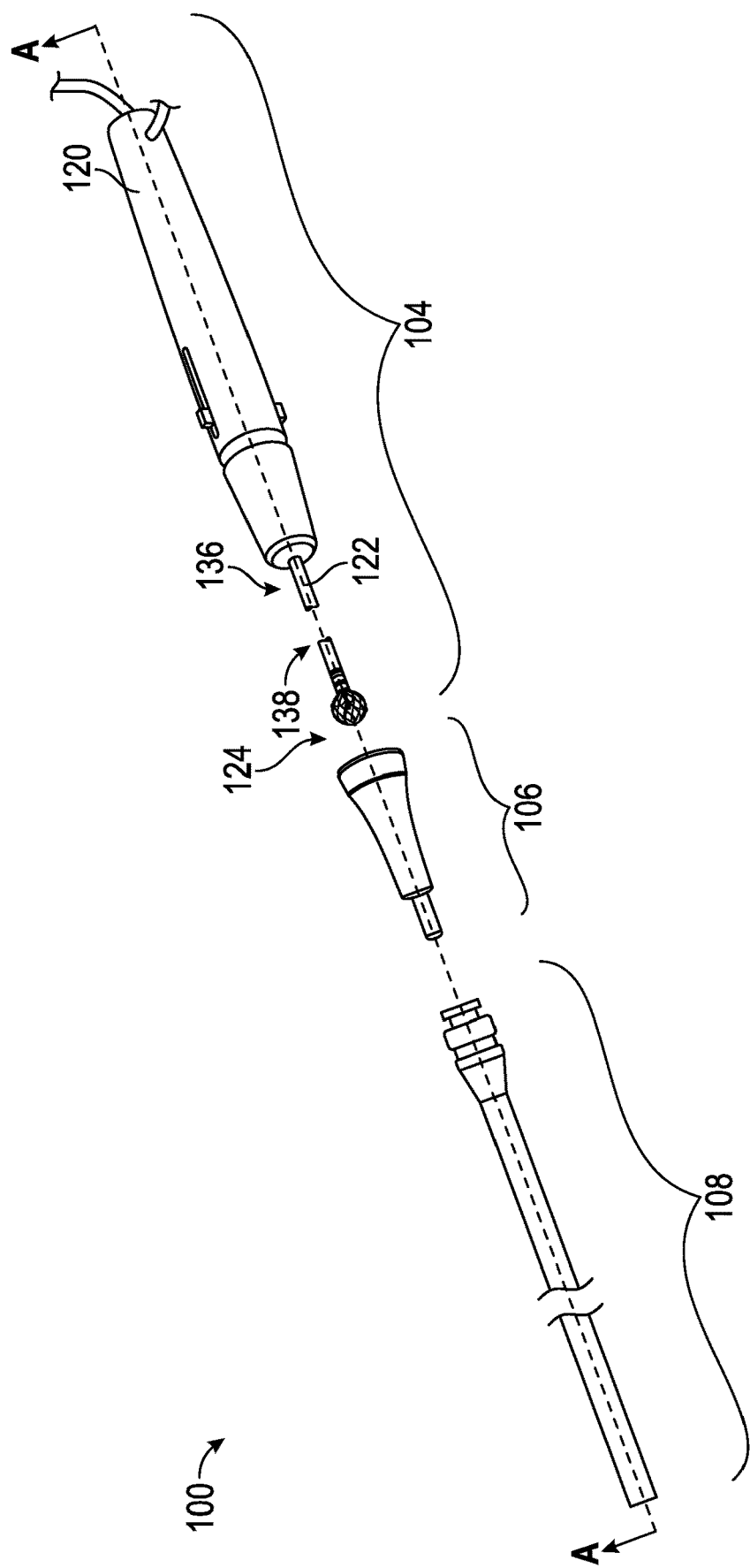
FIG. 1 is a perspective view of a system including a catheter, a sheath, and an insertion sleeve.

Referring now to FIG. 1, a system 100 can include a catheter 104, an insertion sleeve 106, and a sheath 108. The catheter 104 can include a handle 120, a catheter shaft 122, and an expandable tip 124. The handle 120 can be disposed along a proximal portion 136 of the catheter shaft 122, and the expandable tip 124 can be disposed along a distal portion 138 of the catheter shaft 122. In general, the expandable tip 124 can be resiliently flexible between an expanded stated and a compressed state and, in the expanded state, a maximum radial dimension of the expandable tip 124 can exceed a maximum radial dimension of a distal portion of the catheter shaft 122 and a maximum radial dimension of the sheath 108. As used herein, the expanded state of the expandable tip 124 includes a state of the expandable tip 124 in the absence of an externally applied force. In exemplary uses, the expandable tip 124 in the expanded state can be used for one or more of diagnosis and treatment at a site within the patient's body. As a specific example, the expandable tip 124 in the expanded state can be used for ablating tissue (e.g., through the delivery of radiofrequency (RF) energy) in a cardiac chamber of the patient.

In use, the expandable tip 124 can be delivered to a site within the patient's body by moving the expandable tip 124 through the insertion sleeve 106 to compress the expandable tip 124 from the expanded state to the compressed state and moving the expandable tip 124 in the compressed state through the sheath 108 and into vasculature of the patient. For example, as described in greater detail below, movement of the expandable tip 124 of the catheter 104 relative to the insertion sleeve 106 can result in compressing the expandable tip 124 from the expanded state to the compressed state with a reduced likelihood of unintended radial expansion (e.g., bulging). In general, such reduced likelihood of unintended radial expansion can make insertion of the expandable tip 124 easier for the physician and, further or instead, can reduce the likelihood of damage to the expandable tip 124 during insertion. Additionally, or alternatively, as further described in greater detail below, application of force at an angle to the expandable tip 124 can be useful for reducing an overall longitudinal dimension of the insertion sleeve 106, which can be useful for reducing the impact of the insertion sleeve 106 on a usable length of the catheter 104 in instances in which the insertion sleeve 106 remains disposed about the catheter shaft 122 through a medical procedure.

Figure 2:
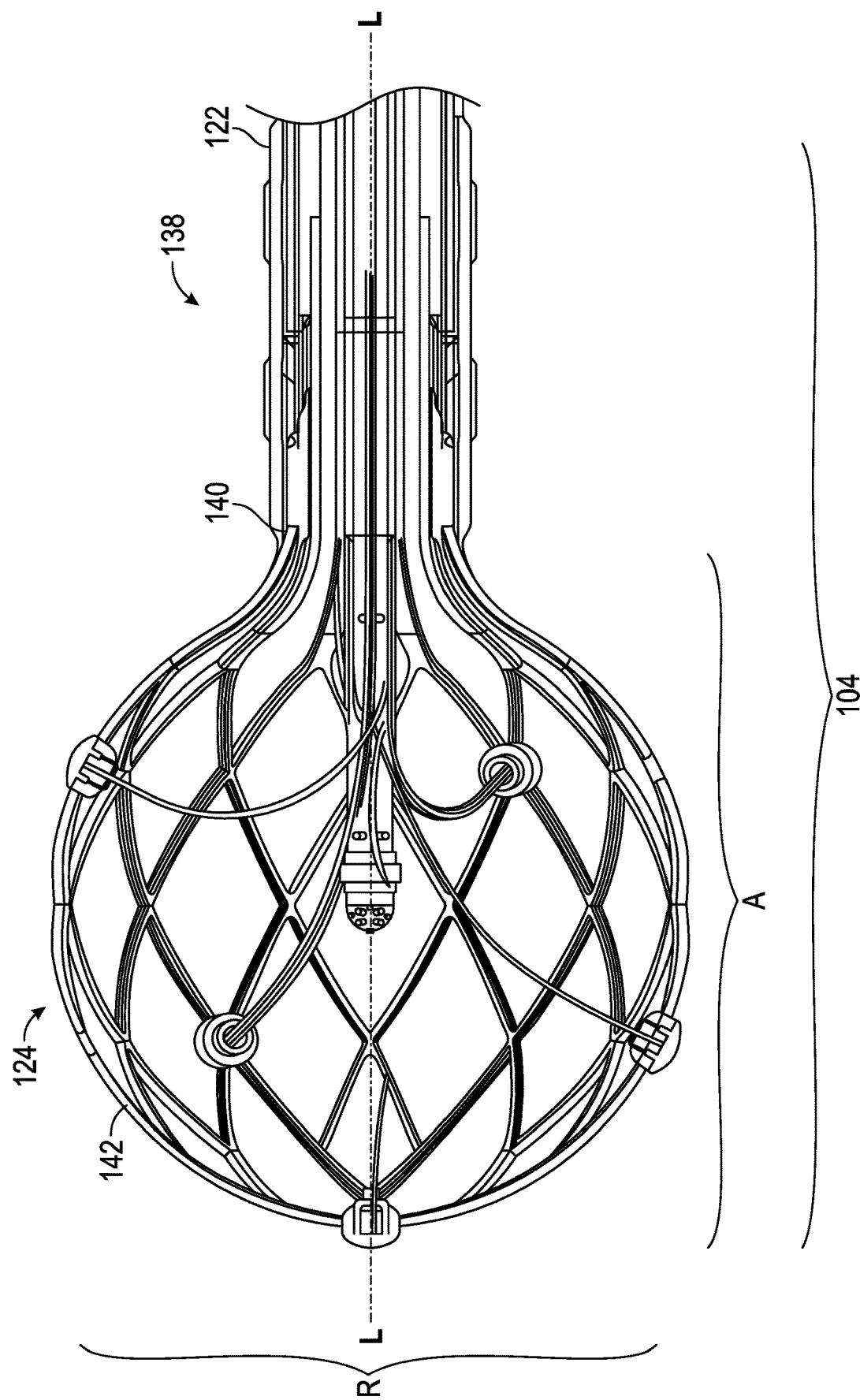
FIG. 2 is a cross-sectional perspective view of an expandable tip of the catheter along cross-section A-A of FIG. 1.

Referring now to FIGS. 1 and 2, the expandable tip 124 can have an axial dimension "A" and a radial dimension "R." The axial dimension "A" can be along a direction substantially parallel to a longitudinal axis "L-L" (e.g., a center axis) defined by the catheter shaft 122, and the radial dimension "R" can be perpendicular to the longitudinal axis "L-L" defined by the catheter shaft 122. In general, application of an axial force to the expandable tip 124 in the distal direction and/or application of a radial force to the expandable tip 124 can facilitate compressing the expandable tip 124 while application of an axial force in the proximal direction can result in the expandable tip 124 resisting compression (e.g., through unintended expansion). Accordingly, the insertion sleeve 106 can engage the expandable tip 124 to apply a force at an angle, which as compared to force applied by an insertion sleeve having a constant diameter, applies less force on the expandable tip 124 in the proximal direction. As used herein, a force applied at an angle to the expandable tip 124 shall be understood to be a net force having a radial component greater than or equal to an axial component exerted on the expandable tip 124. More specifically, a force applied at an angle to the expandable tip 124 shall be understood to be a net force normal to a tangent of a surface of the expandable tip 124 and oriented at an angle greater than or equal to about 45 degrees with respect to an axial direction parallel to the axial dimension "A." In general, the expandable tip 124 can be resiliently flexible between the expanded state and the compressed state such that one or more of the radial dimension "R" and the axial dimension "A" of the expandable tip 124 changes between the expanded state and the compressed state upon application of the force to the expandable tip 124 at an angle. For example, the force applied to the expandable tip 124 at an angle can reduce the radial dimension "R" of the expandable tip 124 such that the expandable tip 124 is movable through the insertion sleeve 106 and through the sheath 108 for insertion into the patient's body.

The expandable tip 124 can include a coupling portion 140 and a deformable portion 142. The coupling portion 140 can be fixed (e.g., through direct or indirect coupling) relative to the catheter shaft 122. The deformable portion 142 can extend in a direction distal to the one or more of the coupling portion 140 and the catheter shaft 122. In response to changes in force applied to the expandable tip 124, the resilient flexing of the expandable tip 124 between the expanded state and the compressed state can include a change in shape of deformable portion 142 of the expandable tip 124.

The expandable tip 124 can include one or more electrodes useful for diagnosis, treatment, or both at a target site in the patient's body. In general, expandability of the expandable tip 124 beyond dimensions of the catheter shaft 122 can facilitate placement of the one or more electrodes beyond dimensions of the catheter shaft 122 at the site of a medical procedure. Such placement of one or more electrodes can be useful, for example, for creating large lesions during an ablation treatment.

In certain implementations, the expandable tip 124 can be a continuous structure that acts as one electrode in a monopolar electrode configuration (e.g., in a configuration with one or more return electrode pads positioned external to the patient's body). In such implementations, the insertion sleeve 106 can facilitate delivery of a relatively large (e.g., as compared to a maximum radial dimension of the catheter shaft 122) ablation electrode to a treatment site for the formation of large lesions. As an example, a material for forming the expandable tip 124 can include nitinol (nickel-titanium), which is repeatably and reliably flexible between the expanded state and the compressed state. Continuing with this example, it should be appreciated that ablation energy can be delivered through the nitinol forming the deformable portion 128 for delivery to tissue to create lesions.

Additionally, or alternatively, the deformable portion 128 can include an arrangement of joints and struts that are flexible relative to one another as the expandable tip 124 moves between the expanded state and the compressed state. Blood and/or saline can pass through the openings defined by the joints and struts to cool the expandable tip 124 during a medical procedure. For example, the expandable tip 124 can have greater than about 50 percent open area and less than about 95 percent open area (e.g., about 80 percent open area).

In certain implementations, at least the deformable portion 128 of the expandable tip 124 can be self-expandable such that the deformable portion 128 returns to the expanded state upon removing or decreasing a compressive force exerted on the deformable portion 128. As a more specific example, the deformable portion 128 can be self-expandable such that the deformable portion 128 moves from the compressed state to the expanded state upon exiting the sheath 108 positioned in the body.

The expandable tip 124 in the expanded state can be based on the size of an anatomic structure in which the expandable tip 124 will be used in the expanded state within the patient. For example, in implementations in which the expandable tip 124 is used for diagnosis and/or treatment of cardiac conditions, the expandable tip 124 can have an outer diameter of greater than about 4 mm and less than about 16 mm (e.g., about 8 mm). It should be appreciated that the type of material and thickness of the material forming the expandable tip 124 can be a function of the flexibility required to flex the expandable tip 124 between the expanded state and the compressed state. Thus, for example, in implementations in which the expandable tip 124 is used for one or more of diagnosis and treatment of cardiac conditions and it is desirable to deliver the expandable tip 124 into vasculature of the patient through the sheath 108 having an 8 Fr gauge, the expandable tip 124 can be formed of one or more metals (e.g., nitinol) having a thickness of greater than about 0.07 mm and less than about 0.25 mm (e.g., about 0.17 mm).

The catheter shaft 122 can be formed of any of various different biocompatible materials that provide the catheter shaft 122 with sufficient sturdiness for moving the expandable tip 124 relative to the insertion sleeve 106 and the sheath 108, as described in greater detail below, but also sufficient flexibility to allow the catheter shaft 122 to be navigated through blood vessels of a patient.

Figure 3:
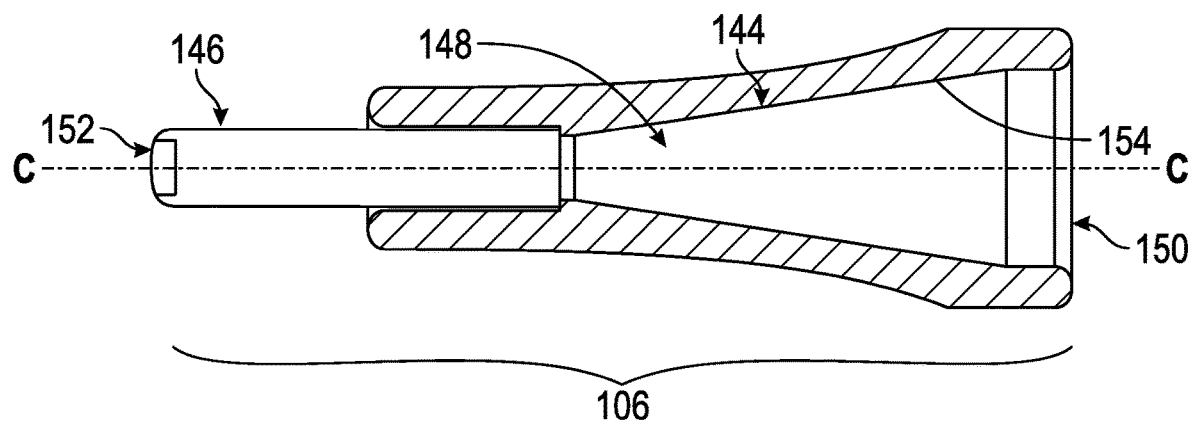
FIG. 3 is a cross-sectional view of the insertion sleeve of FIG. 1 along cross-section A-A of FIG. 1.

Referring now to FIGS. 1 and 3, the insertion sleeve 106 can include a tapered portion 144 and an elongate tube 146 coupled (e.g., directly or indirectly) to one another to define at least a portion of a sleeve lumen 148 extending from a proximal opening 150 to a distal opening 152 defined by the insertion sleeve 106. At least a portion of the insertion sleeve 106 can be formed of any one or more of various different materials that are chemically resistant, semi-rigid, and readily suitable to a variety of known manufacturing techniques. By way of example, and not limitation, at least a portion of the insertion sleeve 106 can be formed of one or more of high density polyethylene (HDPE), polytetrafluoroethylene (PTFE), and the like.

In general, the proximal opening 150 can have a first open area to receive at least a portion of the expandable tip 124 in the expanded state, and the distal opening 152 can have a second open area less than the first open area. In use, the expandable tip 124 can be pushed distally into the insertion sleeve 106 through the proximal opening 150 and, through further distal movement through the insertion sleeve 106, the expandable tip 124 can be pushed out of the insertion sleeve 106 through the distal opening 152. As described in greater detail below, further distal movement of the expandable tip 124 in the compressed state beyond the distal opening 152 can deliver the expandable tip 124 into the sheath 108 for introduction, ultimately, into the vasculature of the patient.

The tapered portion 144 of the insertion sleeve 106 can include, for example, a tapered surface 154 defining at least a portion of the sleeve lumen 148. In general, the tapered surface 154 can decrease the cross-sectional area of the sleeve lumen 148 in a direction from the proximal opening 150 toward the distal opening 152. Thus, as the expandable tip 124 is moved in the direction from the proximal opening 150 toward the distal opening 152, at least a portion of the expandable tip 124 can slide along the tapered surface 154 such that the tapered surface 154 applies force to the expandable tip 124 at an angle to compress the expandable tip 124 from the expanded state to the compressed state.

In general, the application of force to the expandable tip 124 at an angle can advantageously reduce the likelihood of unintended deformation of the expandable tip 124 as the expandable tip 124 is delivered into the body of the patient.

Unintended deformation can be caused by simultaneously applying an inward radial force, which promotes compression of the expandable tip 124, and a proximal axial force, which resists compression of the expandable tip 124. The force applied to the expandable tip 124 along the tapered surface 154 can result in a distribution of force in which a radial component of the applied force exceeds a first compressive force required to deform the expandable tip 124 in the radial dimension "R" of the expandable tip 124 while an axial component of the applied force is less than a second compressive force required to deform the expandable tip 124 in the axial dimension "A" of the expandable tip 124. Accordingly, in such instances, the result of the force applied to the expandable tip 124 can be a reduction in the size of the expandable tip 124 in the radial dimension "R" such that the expandable tip 124 can be introduced into the sheath 108.

The tapered surface 154 can, for example, define a monotonically decreasing area along at least a portion of the tapered portion 144 of the insertion sleeve 106. Additionally, or alternatively, the tapered surface 154 can be substantially symmetric (e.g., substantially frusto-conical) about a plane extending through the proximal opening 150 and the distal opening 152. Such symmetry can be useful for substantially symmetric application of force about a circumference of the expandable tip 124. In general, substantially uniform application of force around the circumference of the expandable tip 124 can be useful for reducing the likelihood of unintended deformation of the expandable tip 124 as the expandable tip 124 is slid along the tapered surface 154.

In general, the size of an included angle θ between the tapered surface 154 and a center axis "C-C" defined by the sleeve lumen 148 can be bounded by considerations related to reducing the likelihood of unintended deformation and considerations related to an overall axial length of the insertion sleeve 106. For example, the included angle θ can be less than a first threshold at which the angled force applied to the expandable tip 124 results in unintended deformation of a portion of the expandable tip 124. Continuing with this example, the included angle θ can be greater than a second threshold, different from the first threshold, limited by considerations related to usable length of the catheter 104. That is, while the included angle θ can be made shallow to avoid unintended deformation of the expandable tip 124, such a shallow angle can result in an increase in length of the sleeve 108, which may be undesirable in implementations in which the insertion sleeve 106 remains disposed about the catheter shaft 122 during the medical procedure.

In implementations in which the tapered surface 150 is substantially frusto-conical, an included angle θ between the tapered surface 154 and the center axis "C-C" defined by the sleeve lumen 148 can be greater than about 4 degrees and less than about 45 degrees. It should be appreciated that this range of angles can be useful for controlling deformation of expandable tip 124 in instances in which, for example, the expandable tip 124 is substantially spherical. As used herein, a substantially spherical shape should be understood to include a shape having at least a hemisphere (e.g., at least a distal hemisphere) lying within a range of the larger of about ±1 mm or about ±25% of a nominal radius from a center point.

In some implementations, at least a portion of the expandable tip 124 can be proximally and distally movable into, through, and beyond the insertion sleeve 106. For example, the expandable tip 124 can be moved distally into, through, and beyond the insertion sleeve 106 such that the expandable tip 124 extends beyond the distal opening 152, and the expandable tip 124 can be retracted proximally back into, through, and beyond the distal opening 152 and withdrawn from the insertion sleeve 106. By comparison, however, an insertion sleeve having a constant diameter similar to that of the sheath 108 can exert forces on the expandable tip 124 that limit or prevent movement of the expandable tip 124 in a distal direction into such a cylindrical sleeve. Accordingly, it should be appreciated that, as compared to a cylindrical sleeve, the ability to move the expandable tip 124 proximally and distally into, through, and beyond the insertion sleeve 106 can, for example, reduce the need to pre-mount the insertion sleeve 106 about the catheter shaft 122. For example, because the expandable tip 124 is proximally and distally movable into, through, and beyond the insertion sleeve 106, the insertion sleeve 106 can be moved in a proximal direction over the expandable tip 124 (e.g., just prior to use) to mount the insertion sleeve 106 for use as part of an insertion procedure. Additionally, or alternatively, the ability to move the expandable tip 124 proximally and distally into, through, and beyond the insertion sleeve 106 can useful for starting the insertion process over, if necessary.

In general, the elongate tube 146 can extend from the tapered portion 144 in a distal direction. The elongate tube 146 can have, for example, a smaller maximum outer dimension than an inner dimension of the sheath 108 such that the elongate tube 146 can be inserted into the sheath 108, as described in greater detail below. The elongate tube 146 can be substantially rigid to facilitate insertion of the insertion sleeve 106 into the sheath 108 (e.g., by pushing the elongate tube 146 into engagement with the sheath 108). Additionally, or alternatively, the outer surface of the elongate tube 146 can be tapered in the distal direction to facilitate moving the elongate tube 146 through a valve 170 (FIG. 4) of the sheath 108 with little to no unintended backflow of pressurized fluid from the sheath 108 as the insertion sleeve 106 is mated with the sheath 108.

Figure 4:
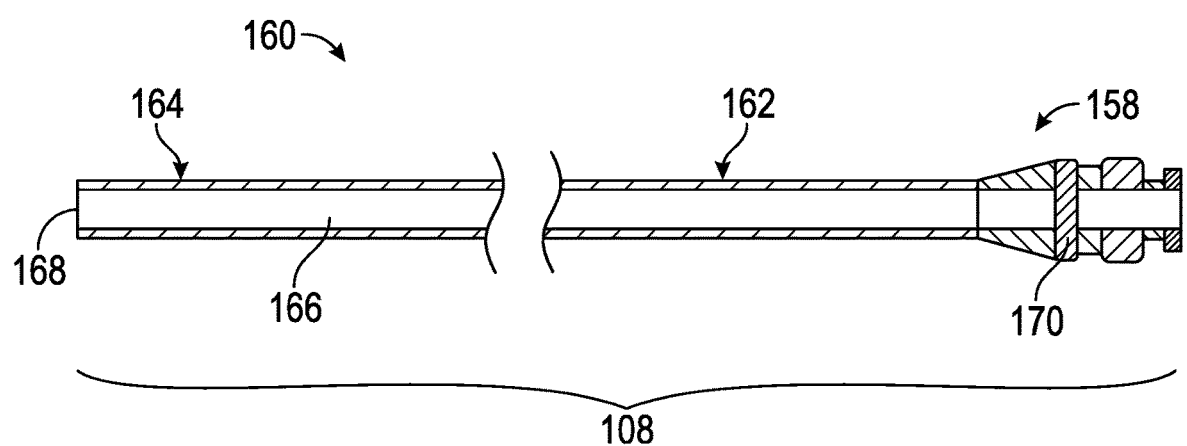
FIG. 4 is a cross-sectional view of the sheath of FIG. 1 along cross-section A-A of FIG. 1.

Referring now to FIGS. 1 and 4, the sheath 108 can include a hub 158 and an elongate shaft 160, the elongate shaft 160 having a proximal portion 162 and a distal portion 164. The hub 158 can be coupled (e.g., directly or indirectly coupled) to the proximal portion 162 of the elongate shaft 160. In general, the sheath 108 can include one or more of an introducer sheath, a steerable sheath, and a fixed curve sheath.

The elongate shaft 160 can define a sheath lumen 166 extending from the proximal portion 162 to the distal portion 164 of the elongate shaft 160. The distal portion of 164 of the elongate shaft 160 can, additionally or alternatively, define an access orifice 168 in fluid communication with the sheath lumen 166. The elongate shaft 160 can, for example, have an 8 Fr (e.g., about 2.7 mm) gauge. The 8 Fr gauge is a standard size and, therefore, familiar to medical personnel. Additionally, or alternatively, an 8 Fr gauge can advantageously provide vascular access through a small incision that, as compared to larger incisions required for larger gauges, can heal faster and can be less prone to infection.

The hub 158 can include a valve 170 in fluid communication with the sheath lumen 166. The valve 170 can be, for example, a hemostatic valve. Continuing with this example, the valve 170 can restrict the unintended flow of blood from the patient's body in a proximal direction through the hub 158 as the elongate shaft 160 of the sheath 108 is introduced into vasculature of the patient. In use, the elongate tube 146 (FIG. 3) of the insertion sleeve 106 (FIG. 3) can extend beyond the valve 170 while the insertion sleeve 106 (FIG. 3)

is mated with the sheath 108. It should be appreciated that extending the elongate tube 146 (FIG. 3) beyond the valve 170 can facilitate moving the expandable tip 124 distally past the valve 170 for insertion into the body.

Referring now to FIGS. 5A-F, to perform a medical treatment in the body of the patient, the distal portion 138 of the catheter shaft 122 and, thus, the expandable tip 124 can be introduced into the patient and then delivered to a target site. FIGS. 5A-F schematically illustrate an exemplary method that can be carried out using the system 100 (FIGS. 1-4) to introduce the expandable tip 124 into the patient through the insertion sleeve 106 and the sheath 108. In general, as described in greater detail below, the exemplary method of introducing the expandable tip 124 into the patient can include positioning a distal portion 164 of the sheath 108 in a blood vessel of the patient, moving the insertion sleeve 106 over the expandable tip 124 supported by the catheter shaft 122, mating the insertion sleeve 106 with the sheath 108, and advancing the expandable tip 124 distally through the sheath 108 and into the vasculature of the patient.

Referring now to FIGS. 1-4 and 5A, a distal portion 164 of the sheath 108 can be positioned within a blood vessel of the patient. Examples of blood vessels that can be accessed as part of the exemplary method include, but are not limited to, the femoral vein or artery.

Referring now to FIGS. 1-4 and 5B, the insertion sleeve 106 can be moved (e.g., in a direction coaxial with the longitudinal axis "L-L" of the catheter shaft 122) over the expandable tip 124 supported by the catheter shaft 122. For example, the expandable tip 124 can be pushed in a distal direction into the insertion sleeve 106. Through such distal movement of the expandable tip 124 into the insertion sleeve 106, the tapered surface 154 of the insertion sleeve 106 can compress at least a portion of the expandable tip 124 from the expanded state to the compressed state. For example, as the expandable tip 124 is pushed distally into the insertion sleeve 106, the expandable tip 124 can engage the tapered surface 154 of the insertion sleeve 106 such that the insertion sleeve 106 exerts a force on the expandable tip 124 at an angle to reduce the likelihood of unintended deformation of the expandable tip 124.

Referring now to FIGS. 1-4 and 5C, the insertion sleeve 106 can be mated with (e.g., inserted into) the sheath 108. Mating the insertion sleeve 106 with the sheath 108 can include, for example, positioning a portion (e.g., the elongate tube 146) of the insertion sleeve 106 within the sheath lumen 166 of the sheath 108. Additionally, or alternatively, mating the insertion sleeve 106 with the sheath 108 can include positioning a portion of the insertion sleeve 106 in the sheath lumen 166 at a position distal to the valve 170 of the sheath 108. Continuing with this example, the portion of the insertion sleeve 106 extending to the position distal to the valve 170 can exert a force sufficient to open the valve 170 during the insertion procedure. With the portion of the insertion sleeve 106 in the sheath lumen 166 at a position distal to the valve 170 of the sheath 108, the sheath 108 can block further distal movement of the insertion sleeve 106 relative to the sheath 108 to facilitate properly positioning of the insertion sleeve 106 relative to the sheath 108 during an insertion procedure.

In certain implementations, with the expandable tip 124 collapsed within the insertion sleeve 106, the insertion sleeve 106 can be mated with the sheath 108. It should be understood, however, that the order of collapsing the expandable tip 124 and mating the insertion sleeve 106 with the sheath 108 can be reversed. Thus, for example, in such implementations, the user can insert the insertion sleeve 106 into the sheath 108 and then, with the insertion sleeve 106 mated with the sheath 108, advance the expandable tip 124 distally into the insertion sleeve 106.

Referring now to FIGS. 1-4 and 5D, with the expandable tip 124 disposed in the sheath 108, the insertion sleeve 106 can be retracted (e.g., moved in a proximal direction relative to the sheath 108, and the expandable tip 124 can be advanced distally through the sheath 108 and into the vasculature of the patient.

In certain implementations, the expandable tip 124 can be collapsible from the expanded state to the compressed state through both distal movement and proximal movement of the expandable tip 124 through the insertion sleeve 106. In such implementations, therefore, the expandable tip 124 can be retracted proximally from the sheath lumen 166 and into the insertion sleeve 106 to collapse the expandable tip from the expanded state to the compressed state. It should be understood that retraction of the expandable tip 124 into the insertion sleeve 106 from the sheath lumen 166 can be useful, for example, for starting the insertion process over.

Referring now to FIGS. 1-4 and 5E, the expandable tip 124 can be extended distally beyond the access orifice 168 of the sheath 108 such that the expandable tip 124 can expand (e.g., self-expand) from the compressed state to the expanded state. In the expanded state, the expandable tip 124 can be moved to a target site and a medical procedure can be performed. In general, the medical procedure can be any one or more of various different diagnostic and treatment procedures. Thus, for example, the medical procedure can be any of various different medical procedures associated with at least one of diagnosis and treatment of a cardiac condition, and, accordingly, the expandable tip 124 can be positioned in a cardiac chamber of the patient.

In certain implementations, the insertion sleeve 106 can be left surrounding the proximal portion 136 of the catheter shaft 122 throughout the remainder of the treatment. In some implementations, the insertion sleeve 106 can be removed from the catheter shaft 122 while the at least one portion of the expandable tip 124 is in the vasculature of the patient. For example, the insertion sleeve 106 can include a breakaway portion that can be removed to remove the insertion sleeve 106 from the catheter shaft 122.

While certain implementations have been described, other implementations possible.

As an example, while the expandable tip 124 has been described as being self-expandable from the compressed state to the expanded state, the expandable tip 124 can also, or instead, be mechanically actuated to expand from the compressed state to the expanded state. Such mechanical actuation can include, for example, a wire coupled to a distal portion of the expandable tip 124. In such instances, the expandable tip 124 can be expanded from the compressed state to the expanded state by pulling the wire in a proximal direction.

As another example, while the insertion sleeves have been described as being used to deliver a catheter including an expandable tip, it should be appreciated that the insertion sleeves of the present disclosure can additionally, or alternatively, be used to deliver other types of catheters into a sheath. As an example, the insertion sleeves of the present disclosure can be used to deliver a catheter formed of a plurality of splines (e.g., in the shape of a basket, in an open arrangement, or a combination thereof), such as catheters commonly used for mapping.

The method steps of the implementations described herein are intended to include any suitable method of causing such method steps to be performed, consistent with the patentability of the following claims, unless a different meaning is expressly provided or otherwise clear from the context. So, for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. A method of inserting a catheter into vasculature of a patient, the method comprising:
    positioning a distal portion of a sheath in a blood vessel of the patient such that a proximal portion of the sheath remains outside the patient, wherein the proximal portion of the sheath comprises a valve in fluid communication with a lumen of the sheath;
    moving an insertion sleeve proximally over an expandable tip supported by a catheter shaft, the proximal movement of the insertion sleeve compressing at least one portion of the expandable Lip from an expanded state to a compressed state along a tapered surface of the insertion sleeve, wherein an angle between the tapered surface and a center axis of the insertion sleeve is greater than about 4 degrees and less than about 45 degrees;
    inserting the insertion sleeve into the sheath;
    mating the insertion sleeve with the proximal portion of the sheath at the valve such that the insertion sleeve remains entirely outside of the patient and a distal portion of the insertion sleeve is positioned within the lumen of the sheath distal of the valve;
    advancing the expandable tip distally beyond the insertion sleeve and into the sheath; and
    retracting the insertion sleeve from the sheath.

2. The method of claim 1, wherein the insertion sleeve is mated with the sheath with the expandable tip disposed in the insertion sleeve in the compressed state.

3. The method of claim 1, wherein the at least one portion of the expandable tip in the expanded state has a maximum radial dimension greater than a maximum inner radial dimension of the sheath.

4. The method of claim 1, wherein the at least one portion of the expandable tip is resiliently flexible between the expanded state and the compressed state in response to addition and removal of external force applied to the at least one portion of the expandable tip.

5. The method of claim 1, wherein the insertion sleeve defines a proximal opening and a distal opening, and the proximal opening is larger than the distal opening.

6. The method of claim 5, wherein the at least one portion of the expandable tip is collapsible from the expanded state to the compressed state through both distal movement of the expandable tip through the proximal opening of the insertion sleeve and through proximal movement of the expandable tip through the distal opening of the insertion sleeve.

7. The method of claim 1, wherein, with the distal portion of the insertion sleeve positioned within the lumen of the sheath distal of the valve, the sheath blocks further distal movement of the insertion sleeve.

8. The method of claim 1, further comprising advancing the expandable tip distally beyond the sheath, wherein advancing the expandable tip distally beyond the sheath includes expanding the at least one portion of the expandable tip from the compressed state to the expanded state.

9. The method of claim 8, wherein the at least one portion of the expandable tip is self-expandable from the compressed state to the expanded state.

10. The method of claim 1, wherein the tapered surface of the insertion sleeve is substantially frusto-conical.

11. The method of claim 1, further comprising removing the insertion sleeve from the catheter shaft while the at least one portion of the expandable tip is in the vasculature of the patient.

12. The method of claim 11, wherein the insertion sleeve includes a break-away portion and removing the insertion sleeve from the catheter shaft includes removing the break-away portion from the insertion sleeve.

13. A system comprising:
    a catheter including a shaft and a generally spherical expandable tip disposed along a distal portion of the shaft, at least one portion of the expandable tip resiliently flexible between an expanded state and a compressed state;
    a sheath defining a sheath lumen and having a proximal portion comprising a valve in fluid communication with the sheath lumen, wherein the proximal portion is configured to remain outside of a patient when a distal portion of the sheath is inserted into a blood vessel of a patient, and wherein the at least one portion of the expandable tip, in the compressed state, is movable through the sheath lumen; and
    an insertion sleeve including (a) a tapered surface defining at least a portion of an insertion sleeve lumen and (b) an elongate tube,
        wherein the insertion sleeve is configured to be inserted into the sheath to engage with the proximal portion of the sheath at the valve such that (a) a distal portion of the elongate tube is positioned within the sheath lumen distal of the valve and (b) the insertion sleeve remains entirely outside of the patient when the distal portion of the sheath is inserted into the blood vessel, wherein the at least one portion of the expandable tip is movable into engagement with the tapered surface of the insertion sleeve, and wherein the engagement with the tapered surface of the insertion sleeve compresses the at least one portion of the expandable tip from the expanded state to the compressed state as the at least one portion of the expandable tip is moved through the insertion sleeve lumen in a direction toward the sheath lumen.

14. The system of claim 13, wherein the tapered surface of the insertion sleeve is substantially frusto-conical.

15. The system of claim 13, wherein the insertion sleeve defines a proximal opening and a distal opening, the proximal opening having a first open area to receive the at least one portion of the expandable tip in the expanded state and the distal opening having a second open area less than the first open area.

16. The system of claim 13, wherein the at least one portion of the expandable tip is proximally and distally movable through the insertion sleeve.

17. The system of claim 13, wherein the elongate tube is tapered in a distal direction.

* * * * *